(12) United States Patent
Veasey et al.

(10) Patent No.: US 8,961,472 B2
(45) Date of Patent: Feb. 24, 2015

(54) METHOD OF ASSEMBLY OF DRUG DELIVERY DEVICES

(75) Inventors: Robert Veasey, Leamington Spa (GB); Steven Wimpenny, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1823 days.

(21) Appl. No.: 11/680,638

(22) Filed: Mar. 1, 2007

(65) Prior Publication Data

US 2008/0015511 A1   Jan. 17, 2008

Related U.S. Application Data

(63) Continuation of application No. PCT/EP2005/009217, filed on Aug. 26, 2005.

(30) Foreign Application Priority Data

Sep. 2, 2004 (EP) ..................................... 04020877

(51) Int. Cl.
*A61M 5/00* (2006.01)
*A61M 5/315* (2006.01)
*A61M 5/24* (2006.01)

(52) U.S. Cl.
CPC .............. *A61M 5/31593* (2013.01); *A61M 5/24* (2013.01); *A61M 5/31541* (2013.01); *A61M 5/31551* (2013.01); *A61M 5/31558* (2013.01); *A61M 5/31561* (2013.01); *A61M 5/31585* (2013.01); *A61M 2205/581* (2013.01); *A61M 2205/582* (2013.01)
USPC ........................................................ 604/207

(58) Field of Classification Search
USPC .......... 604/181, 187, 218–234, 207–211, 110
See application file for complete search history.

(56) References Cited

U.S. PATENT DOCUMENTS

| | | | | |
|---|---|---|---|---|
| 5,017,190 A | * | 5/1991 | Simon et al. ................... | 604/207 |
| 5,226,895 A | * | 7/1993 | Harris ............................ | 604/208 |
| 5,281,198 A | * | 1/1994 | Haber et al. ..................... | 604/86 |
| 5,626,566 A | * | 5/1997 | Petersen et al. ................ | 604/208 |
| 5,688,251 A | * | 11/1997 | Chanoch ........................ | 604/208 |
| 6,364,865 B1 | * | 4/2002 | Lavi et al. ...................... | 604/411 |
| 6,569,126 B1 | | 5/2003 | Poulsen et al. | |
| 7,635,348 B2 | * | 12/2009 | Raven et al. ................... | 604/111 |

FOREIGN PATENT DOCUMENTS

| | | |
|---|---|---|
| EP | 0 937 471 | 8/1999 |
| WO | 98/13085 | 4/1998 |
| WO | WO 2004/078240 | 9/2004 |

* cited by examiner

*Primary Examiner* — Bhisma Mehta
*Assistant Examiner* — Bradley Osinski
(74) *Attorney, Agent, or Firm* — McDonnell Boehnen Hulbert & Berghoff LLP

(57) ABSTRACT

The present invention relates to a method for the assembly of drug delivery devices, in particular of pen-type drug delivery devices, having a dose dial mechanism and a drive mechanism, enabling the administration of medicinal products from a multidose cartridge and the drug delivery devices obtainable according to the said method.

18 Claims, 7 Drawing Sheets

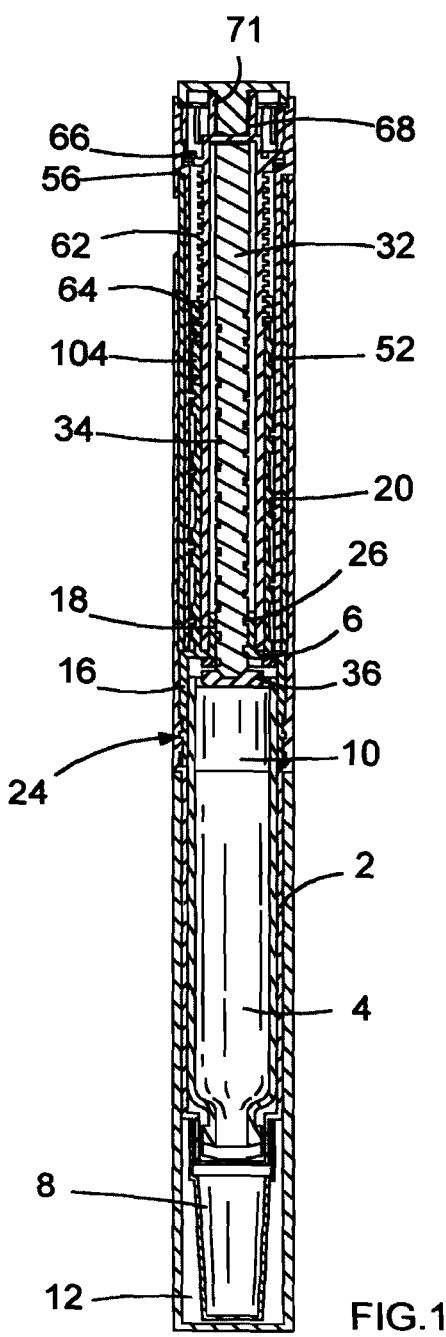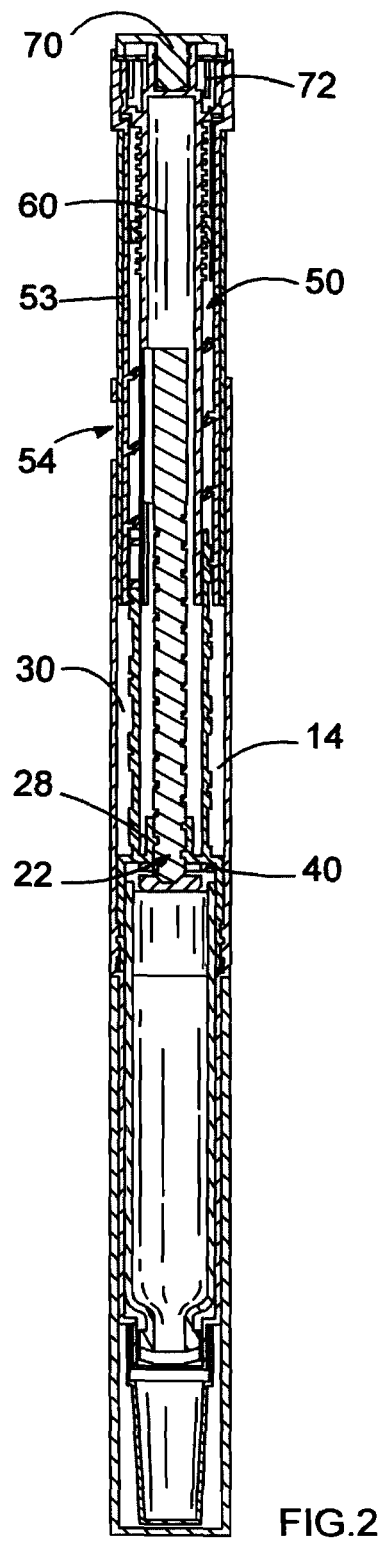

METHOD OF ASSEMBLY OF DRUG DELIVERY DEVICES

The present invention relates to a method for the assembly of drug delivery devices, in particular of pen-type drug delivery devices, having a dose dial mechanism and a drive mechanism, enabling the administration of medicinal products from a multidose cartridge and the drug delivery devices obtainable according to the said method.

BACKGROUND OF THE INVENTION

Such drug delivery devices have application where regular injection by persons without formal medical training occurs, i.e., patients. This is increasingly common amongst those having diabetes where self-treatment enables such persons to conduct effective management of their diabetes.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. In the case of those with diabetes, many users will be physically infirm and may also have impaired vision requiring the drive mechanism to have low dispensing force and an easy to read dose setting display. In case of disposable devices, the device should be cheap to manufacture and easy to dispose of (preferably being suitable for recycling). To meet these requirements the number of parts required for assembling the device and the number of material types the device is made from need to be kept to a minimum.

User operated drug delivery devices and their methods of assembly are well known within the medical field.

Most prior art technologies have the disadvantage that the drug delivery devices comprise a two part housing, which weakens the mechanical stability of the device, e.g., between cartridge and drive mechanism, which may result in unsatisfactory user safety issues.

U.S. Pat. No. 5,226,895 discloses a syringe comprising a unitary housing for holding a container of liquid and a plunger rod having a non-cylindrical cross-section. The syringe further comprises a collar received within the housing having a non-cylindrical cross-section corresponding to the piston rod. The dose dial mechanism of the disclosed concept is mechanically engaged with the unitary housing.

WO9813085A1 discloses a needle-less injector device having a unitary housing, comprising a chamber for the drug to be applied, a liquid outlet, a dispensing member, an impacting member, a drive means, and a pressure sensor, where the chamber, the liquid outlet and the drive means are immobile with respect to the housing. This device does not comprise a dose dial mechanism.

SUMMARY OF THE INVENTION

Surprisingly, it was found that the use of a unitary housing in the method of assembling a drug delivery device according to instant invention overcomes the above shortcomings by increasing the mechanical and structural stability of the device. Therefore, the method according to instant invention provides a drug delivery device having a reduced number of joints making assembly of the device more efficient and providing a drug delivery device having increased user comfort and safety.

For example, PCT/EP2004/002116, which disclosure content is hereby incorporated by reference, discloses a certain type of a drive mechanism, a dose dial mechanism, and a drug delivery mechanism particularly suitable for instant method of assembly.

BRIEF DESCRIPTION OF THE DRAWINGS

FIG. 1 shows a sectional view of a first embodiment of the drug delivery device in accordance with the present invention in a first, cartridge full, position.

FIG. 2 shows a sectional view of the drug delivery device of FIG. 1 in a second, maximum first dose dialed, position.

DETAILED DESCRIPTION OF THE INVENTION

Figure 3:
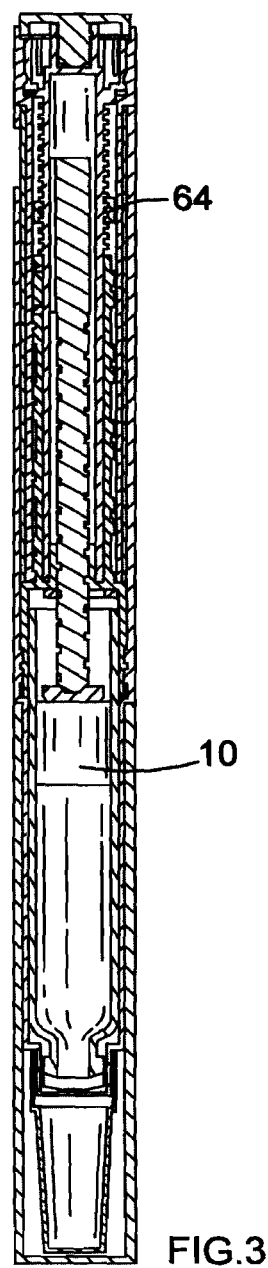
FIG. 3 shows a sectional view of the drug delivery device of FIG. 1 in a third, maximum first dose dispensed, position.

Therefore, it is a first object of instant invention to provide a method of assembling a drug delivery device comprising the steps of a) providing a unitary housing, a cartridge, a drive mechanism, a dose dial mechanism, and optionally a drug delivery mechanism; and b) inserting or introducing the cartridge, the drive mechanism, the dose dial mechanism, and optionally the drug delivery mechanism into the unitary housing, whereby said cartridge, said drive mechanism, and said dose dial mechanism and optionally said drug delivery mechanism are not mechanically engaged with the said unitary housing. In a preferred embodiment, the cartridge is first inserted or introduced into the unitary housing. In another preferred embodiment, one or more of the components of the drug delivery device (such as the cartridge, the drive mechanism, the dose dial mechanism, and/or the drug delivery mechanism or any components thereof) may be pre-assembled and/or are modular allowing them to be introduced or inserted into the unitary housing.

A second object of instant invention is to provide the drug delivery device obtainable by the method of assembly according to instant invention.

The term "drug delivery device" according to meaning of instant invention is a single-dose or multi-dose, disposable or re-usable device designed to dispense a selected dose of a medicinal product, preferably multiple selected doses, more preferred pharmaceutical formulations for subcutaneous or intramuscular administration, most preferred of insulin, growth hormones, heparin (low molecular weight heparin), and their analogues and/or derivatives or any other drug, which is to be administered intramuscularly or subcutaneously. The drug delivery device may be of any shape, e.g.

compact (e.g. non-pen-type) or pen-type. Dose delivery may be provided through a mechanical (optionally manual) or electrical drive mechanism or stored energy drive mechanism, such as a spring, motor, etc. Drug delivery may be provided by an actuation button, switch, knob, etc. Dose selection may be provided by a dose dial mechanism, which may be a manual mechanism or electronic mechanism. Additionally, said device may optionally contain components designed to monitor physiological properties such as blood glucose levels, etc.

Furthermore, the said device may comprise a needle or may be needle-free. In particular preferred embodiment the term drug delivery device shall mean a disposable multi-dose pen-type device having mechanical and manual dose delivery and dose dial mechanisms, which is designed for regular use by persons without formal medical training such as patients. Preferably, the drug delivery device is of the injector-type.

The term "unitary housing" according to instant invention means any drug delivery device outer housing, which covers the cartridge, the drive mechanism, the dose dial mechanism, and optionally the drug delivery mechanism of the drug delivery device.

The term "unitary housing" according to instant invention shall preferably mean an exterior housing ("main housing", "body", "shell"). The unitary housing may be designed to enable the safe, correct, and comfortable handling of the drug delivery device or any of its mechanisms. Usually, it is designed to house, fix, and/or protect any of the inner components of the drug delivery device (e.g., the drive or dose dial mechanism, cartridge, plunger, piston rod) by limiting the exposure to contaminants, such as liquid, dust, dirt, etc. In general, the housing is a one-piece component of tubular ("pen-type") or non-tubular ("non-pen-type") shape, preferably manufactured as one single piece (e.g., moulded, extruded etc.). Usually, the unitary housing serves to house a cartridge from which a number of doses of a medicinal product may by dispensed. Accordingly, the unitary housing may also serve as a cartridge holder and as a drive and dose dial mechanism holder. Preferably, the unitary housing may have one or more openings (windows, apertures) to allow the handling and/or operation of the device.

The term "engaged" according to instant invention shall particularly mean the interlocking of two or more components of the drug delivery device, e.g. a spline or thread connection, preferably the interlocking of helical threads of components ("threadedly engaged").

The term "mechanically engaged" according to instant invention means any engagement of the cartridge, the drive mechanism, the dose dial mechanism, and/or optionally the drug delivery mechanism with the unitary housing by threaded or splined interaction, whereby relative movement with respect to the unitary housing is allowed. Therefore, the term "mechanically engaged" does not mean any press or fit engagement, or the like in order to fix (or hold) the cartridge, the drive mechanism, the dose dial mechanism, and/or optionally the drug delivery mechanism to the unitary housing.

The term "first end" according to instant invention shall mean the proximal end. The proximal end of the device or a component of the device shall mean the end, which is closest to the dispensing end of the device.

The term "second end" according to instant invention shall mean the distal end.

The distal end of the device or a component of the device shall mean the end, which is furthest away from the dispensing end of the device.

The invention will now be described, by way of example only, with reference to the accompanying drawings.

DETAILED DESCRIPTION OF THE EMBODIMENTS

Example 1

Referring to FIGS. 1 to 5 there is seen a drug delivery device assembled in accordance with the first embodiment of the present invention. The device comprises a housing 2 within which are located a cartridge 4 containing a medicinal product, means for setting or selecting the dose of medicinal product to be expelled and means for expelling the selected dose of medicinal product. The housing 2 is generally cylindrical in shape and is divided into two compartments by a web 6 to be described in more detail below. The cartridge 4 is located within a first compartment of the housing 2. The dose setting means and the means for expelling the selected dose of medicinal product are retained, that is held, within a second compartment of the housing 2. An advantage of a one piece housing enclosing the cartridge 4 together with the dose setting and dose expelling means lies in the ease of assembly of the product. This is in part due to the reduced number of components in the pen-type injector. Also, the unitary nature of the housing 2 means that the pen-type injector is more robust.

The cartridge 4 may be secured in position in the first compartment of the housing 2 by any suitable means. A needle unit may be secured to the first end of the cartridge 4. A temporary covering 8 is shown in this position in the Figures. The cartridge 4 is sealed by a displaceable piston 10. Advancing the piston 10 towards the first end of the cartridge 4 causes the medicinal product to be expelled from the cartridge 4 through the needle unit. A cap 12 is provided to cover the needle unit when the injector is not in use. The cap 12 may be releasably secured to the housing 2 by any suitable means.

The dose setting means and the means for expelling the selected dose of medicinal product will now be described in more detail. The web 6 dividing the housing 2 is a part of an insert 14 located within the housing 2. The insert 14 comprises a first cylindrical portion 16 extending from a first side of the web 6 and second and third cylindrical portions 18, 20 extending from a second side of the web 6. The web 6 is provided with a circular opening 22 extending through the web 6.

The first cylindrical portion 16 extends from a periphery of the web 6. The insert 14 is secured to the housing 2 by way of the first cylindrical portion 16 by any suitable means. In the illustrated embodiment features 24 are provided within the housing 2 and on an outer surface of the first cylindrical portion 16 to enable the insert to be a snap fit to the housing 2.

The second cylindrical portion 18 extends a small distance from the second side of the web 6 about a periphery of the opening 22. An internal surface of the second cylindrical portion is provided with a thread 26.

The third cylindrical portion 20 extends substantially within the housing 2 from the second side of the web 6. The diameter of the third cylindrical portion 20 is such that a first channel 28 is formed between an outer surface of the second cylindrical portion 20 and an inner surface of the third cylindrical portion. A second channel 30 is formed between an outer surface of the third cylindrical portion 20 and the housing 2.

A piston rod 32 extends through the opening in the web 6. The piston rod 32 is generally elongate and is provided with a thread 34 extending from a first end of the piston rod 32. The thread 34 of the piston rod 32 engages the thread of the inner surface of the second cylindrical portion 18 of the insert 14. The first end of the piston rod 32 is provided with a pressure foot 36. In use the pressure foot 36 is disposed on the first side of the web 6 to abut the cartridge piston 10.

Ratchet means 40 are located adjacent the web 6 on the first side of the web 6. The ratchet means 40 serve the purpose of allowing the piston rod 32 only to rotate through the insert 14 in a single direction. Due to the unitary housing, the ratchet means can be made larger than in known devices and so is stronger (more rigid).

A dose dial sleeve 50 of generally cylindrical form comprises a first section of first diameter and a second section of second diameter. The first section is located within the second channel 30. An inner surface of the first section and the outer surface of the third cylindrical portion 20 are provided with interengaging features to provide a helical thread 52 between the insert 14 and the dose dial sleeve 50. In the illustrated embodiment this was achieved by a helical track provided on the outer surface of the third cylindrical portion 20 within which a helical rib provided on the inner surface of the dose dial sleeve 50 may run. This enables the dose dial sleeve 50 to rotate about and along the third cylindrical portion 20 of the insert 14.

An outer surface of the first section of the dose dial sleeve 50 is provided with graphics 53. The graphics are typically a sequence of reference numerals. The housing 2 is provided with an aperture or window 54 through which a portion of the graphics, representing a dosage value selected by the user, may be viewed.

The graphics 53 may be applied to the dose dial sleeve 50 by any suitable means. In the illustrated embodiment, the graphics 53 are provided in the form of a printed label encircling the dose dial sleeve 50. Alternatively the graphics may take the form of a marked sleeve clipped to the dose dial sleeve 50. The graphics may be marked in any suitable manner, for example by laser marking.

It is an advantage of this arrangement that the helical thread 52 is formed within the dose dial sleeve between the dose dial sleeve and the insert. As can be seen this means there is no direct route from outside the device to the working surfaces of the helical thread. Should dust or dirt enter the device this will tend to occur between the unitary housing and the dose dial sleeve where there are no working parts with which to interfere. This is not the case for known devices in which a helical thread is formed between the housing and an interior moving surface.

The second section of the dose dial sleeve 50 is preferably of the same outer diameter as the housing 2. Within the dose dial sleeve 50 there is a shoulder 56 between the first section of the dose dial sleeve 50 and the second section of the dose dial sleeve 50.

A drive sleeve 60 of generally cylindrical form comprises a first part of first diameter and a second part of second diameter. A first end of the first part is located within the first channel 28 of the insert 14 in the position shown in FIG. 1. The first part of the drive sleeve 60 may be considered as comprising a first portion aligned with a second portion. More generally in the position shown in FIG. 1 the first portion of the drive sleeve 60 is located between the insert 14 and the piston rod 32 while the second portion is located between the piston rod 32 and the dose dial sleeve 50.

A second end of the piston rod 32 and an internal surface of the drive sleeve 60 are splined together such that no relative rotation may occur between these parts, only longitudinal displacement.

The outer surface of the second portion of the first part of the drive sleeve 60 is provided with a helical thread 62. A nut 64 is provided on the helical thread 62 between the drive sleeve 60 and the dose dial sleeve 50. The dose dial sleeve 50 and the nut 64 are splined together by spline means to prevent relative rotation between the nut 64 and the dose dial sleeve 50.

The second part of the drive sleeve 60 is of larger diameter than the first part of the drive sleeve 60. There is a step 66 between the first part of the drive sleeve 60 and the second part. The second part of the drive sleeve 60 is seated within the second section of the dose dial sleeve 50. The shoulder 56 of the dose dial sleeve 50 and the step 66 of the drive sleeve 60 are adapted to be releasably engagable with one another to form a clutch means. When, as in FIG. 1, the dose dial sleeve 50 and the drive sleeve 60 are not in engagement the dose dial sleeve 50 is able to rotate with respect to the drive sleeve 60. Conveniently, the clutch means comprises a plurality of radially extending longitudinally directed teeth provided respectively on the shoulder 56 of the dose dial sleeve 50 and the step 66 of the drive sleeve 60. When the dose dial sleeve 50 and the drive sleeve 60 are not forced together the respective teeth will ride over one another. Preferably, the radial separation of the respective teeth corresponds to a unit dosage.

The second part of the drive sleeve 60 further comprises a central receiving area 68 having a peripheral recess. A button 70 of generally "T" shaped configuration is provided, the stem of which is retained within the receiving area. The stem of the button 70 is provided with a peripheral bead 71 that is retained in the peripheral recess, the button 70 being able freely to rotate with respect to the drive sleeve 60, but being retained axially therewith.

Clicker means are provided between the second section of the dose dial sleeve 50 and the second part of the drive sleeve 60. In the illustrated embodiment, the internal surface of the second section of the dose dial sleeve 50 is provided with a plurality of longitudinally extending teeth. The radial separation of the teeth preferably corresponds to a unit dosage. The second part of the drive sleeve 60 carries a flexible toothed member 72. Relative rotation between the dose dial sleeve 50 and the drive sleeve 60 will cause the flexible toothed member 72 to ride over the teeth to produce a series of clicks.

In FIG. 1, the injector is provided with a filled cartridge 4. To operate the injector a user must first select a dose. To set a dose the dose dial sleeve 50 is rotated by manipulating the second section of the dose dial sleeve 50 with respect to the housing 2 until the desired dose value is visible through the window 54. This action draws the dose dial sleeve 50 along the second cylindrical portion of the insert 14. The drive sleeve 60 cannot rotate since it is splined to the piston rod 32. The piston rod 32 does not rotate due to the action of the ratchet means 40. The drive sleeve 60 is carried away from the web 6 along the piston rod 32 by the dose dial sleeve 50 as the dose dial sleeve 50 moves out from the housing 2. The relative rotation between the dose dial sleeve 50 and the drive sleeve 60 causes the flexible toothed member 72 to ride over the ridges in the drive sleeve 60 to create a series of clicks. This is an audible confirmation of the dose being dialed.

Since the nut 64 is splined to the dose dial sleeve 50, the relative rotation between the dose dial sleeve 50 and the drive sleeve 60 causes the nut 64 to process along the helical thread 62 of the drive sleeve 60.

Once a desired dose has been set (as shown for example in FIG. 2), to deliver the dose the user depresses the button 70 to urge the button 70 towards the first end of the housing 2. When the button 70 is depressed the second part of the drive sleeve 60 is driven into the second section of the dose dial sleeve 50 to engage the clutch means there between to prevent relative rotation between the dose dial sleeve 50 and the drive sleeve 60. The drive sleeve 60 may still rotate with respect to the button 70. Further longitudinal movement of the button 70 causes the dose dial sleeve 50 (together with the drive sleeve 60) to rotate towards the first end of the injector. Since the piston rod 32 is splined to the drive sleeve 60, the piston rod 32 is also rotated through the insert 14 and the ratchet means 40 towards the first end of the injector, thereby to advance the cartridge piston 10 and expel the desired dose of medicinal product. The piston rod 32 continues to advance until the drive sleeve 60 and dose dial sleeve 50 have returned to their initial positions (FIG. 3).

It can be seen that the dose selecting means and the dose expelling means extend beyond a second end of the housing 2 as the dose is selected and are returned within the housing 2 as the selected dose is expelled.

Figure 4:
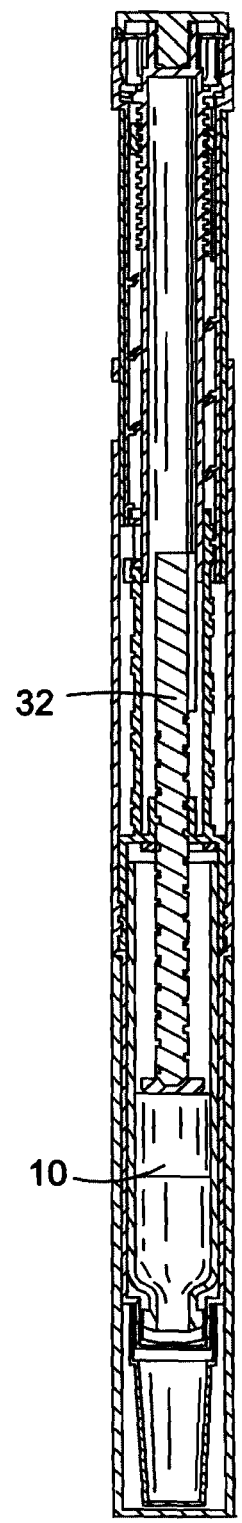
FIG. 4 shows a sectional view of the drug delivery device of FIG. 1 in a fourth, final dose dialed, position.
Figure 5:
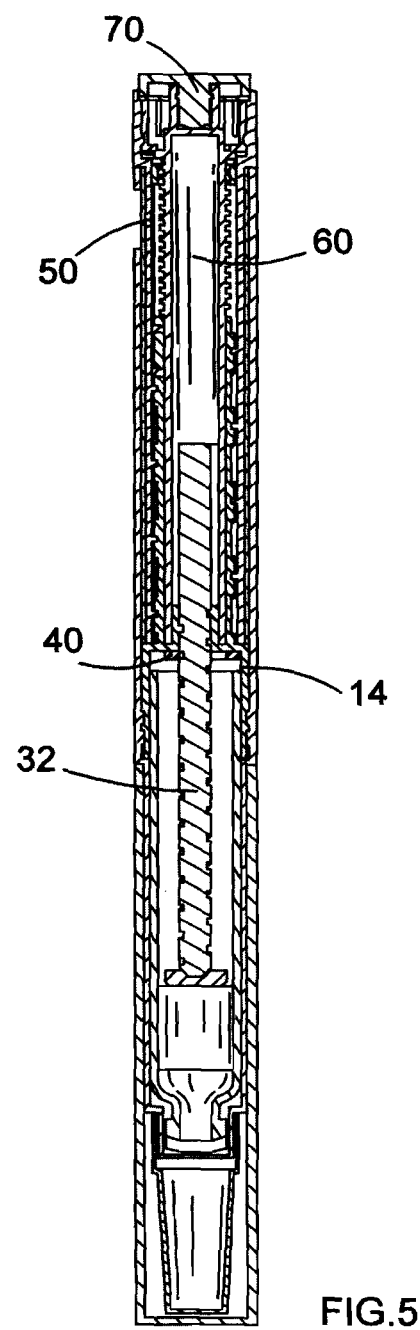
FIG. 5 shows a sectional view of the drug delivery device of FIG. 1 in a fifth, final dose dispensed, position.

Further dosages may be delivered as required. FIG. 4 shows an example of a subsequently selected dosage. It will be noted that the nut 64 has advanced further along the helical thread 62 of the drive sleeve 60. The position of the nut 64 along the helical thread 62 corresponds to the amount of medicinal product remaining in the cartridge 4, such that when the nut 64 reaches the end of the helical thread 62 (in the illustrated embodiment adjacent to the step 66 of the drive sleeve 60) and can rotate no further this corresponds to no medicinal product remaining in the cartridge 4. It will be seen that if a user seeks to select a quantity of medical product greater than that remaining in the cartridge 4, this cannot be done since when the nut 64 stops rotating the dose dial sleeve 50 and the drive sleeve 60 will become locked together preventing rotation of the dose dial sleeve 50 and setting of a larger dose. FIG. 5 shows an injector according to the present invention in which the entire medical product within the cartridge 4 has been expelled.

Figure 6:
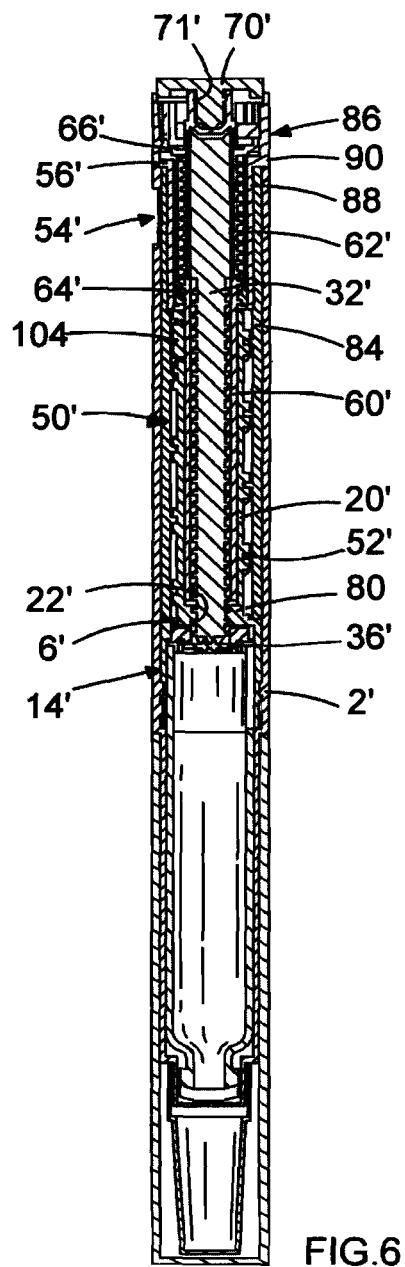
FIG. 6 shows a sectional view of a second embodiment of the drug delivery device in accordance with the present invention.

A second embodiment of the present invention is disclosed in FIG. 6. Like reference numerals are used to refer to like parts as between the first and second embodiments.

The piston rod 32' shown in FIG. 6 has a dual start thread. The piston foot 36' is reversible. This has advantages in manufacture. As can be seen the structure of the insert 14' has been revised. The first side of the web 6' is substantially unchanged. The other side of the web is now provided with a boss 80. A cylindrical portion 20' extends away from the web 6' about a periphery of the boss 80. Threaded opening 22' extends through the web 6' and the boss 80. An end of the cylindrical portion 20' of the insert 14' remote from the web 6' is provided with a stop in the form of a land 104.

The dose dial sleeve 50' is of modified construction. The dose dial sleeve comprises a first cylindrical portion 84 rigidly connected to a second generally cylindrical portion 86. An inner surface of the first cylindrical portion 84 and the outer surface of the cylindrical portion 20' of the insert 14' are provided with interengaging features to provide a helical thread 52' between the insert 14' and the dose dial sleeve 50'. An outer surface of the first cylindrical portion 84 is provided with the dose graphics. The housing 2' is provided with an aperture or window 54' through which a portion of the graphics may be viewed.

The second generally cylindrical portion 86 comprises a first cylindrical section 88 and a second cylindrical section 90. The first section 88 is rigidly keyed to an inner surface of the first portion 84 of the dose dial sleeve 50'. The second section 90 is preferably of the same outer diameter as the housing 2'. Within the dose dial sleeve 50' there is a shoulder 56' between the first section 86 and the second section 90.

A nut 64' is provided on the helical thread 62' between the drive sleeve 60' and the first cylindrical section 88 of the dose dial sleeve 50'. The first cylindrical section 88 and the nut 64' are splined together by spline means to prevent relative rotation between the nut 64' and the dose dial sleeve 50'.

The shoulder 56' of the dose dial sleeve 50' and a step 66' of a drive sleeve 60' are adapted to be releasably engagable with one another to form a clutch means. When, as in FIG. 6, the dose dial sleeve 50' and the drive sleeve 60' are not in engagement the dose dial sleeve 50' is able to rotate with respect to the drive sleeve 60'. Conveniently, the clutch means comprises a plurality of radially extending longitudinally directed teeth provided respectively on the shoulder 56' of the dose dial sleeve 50' and the step 66' of the drive sleeve 60'. When the dose dial sleeve 50' and the drive sleeve 60' are not forced together the respective teeth will ride over one another.

It will be seen that the structure of the drive sleeve 60' has also been modified. The second end of the piston rod 32' is provided with a scooped surface within which a domed part 90 of the drive sleeve 60' may extend. The domed part 90 is centrally located within a second part of the drive sleeve 60' at a first end of the receiving area.

The button 70' is of generally "T" shaped configuration. The stem of the button 70' is retained within the receiving area. The stem of the button 70' is provided with a peripheral bead 71' that is retained in the peripheral recess, the button 70' being able freely to rotate with respect to the drive sleeve 60', but being retained axially therewith.

When the button 70' is depressed the drive sleeve 60' is urged into contact with the dose dial sleeve 50' such that the clutch means are engaged. At the same time, the scooped surface of the piston rod 32' and the domed surface of the drive sleeve approach but do not contact one another. The advantage of this structure is that it enables the overall length of the device to be reduced thereby enabling easier operation of the device when expressing fluid from a cartridge.

Figure 7:
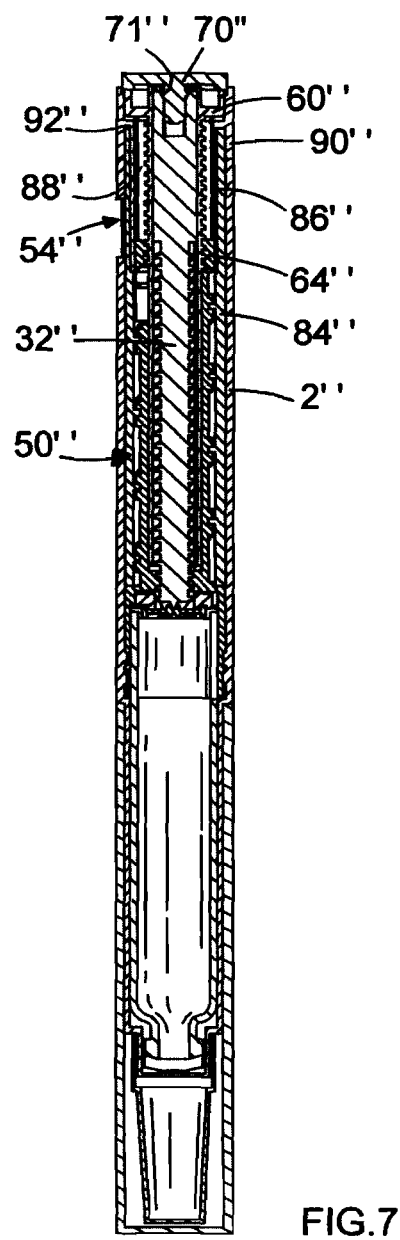
FIG. 7 shows a sectional side view of a third embodiment of the drug delivery device in accordance with the present invention.

A further embodiment of the button 70" and the dose dial sleeve 50" can be seen in FIG. 7. Again like reference numerals are used to refer to like parts. In the embodiment of FIG. 7, the overall length of the device may be reduced still further. The second end of the piston rod 32" is generally U-shaped. The limbs of the U-shape are received within a second part of the drive sleeve 60". A central receiving area of the drive sleeve 60" is defined by limbs (not shown) located in use between the limbs formed on the second end of the piston rod 32". The button 70" is of generally "T" shaped configuration. The stem of the button 70" is retained within the receiving area. The stem of the button 70" is provided with a peripheral bead 71" that is retained in the peripheral recess, the button 70" being able freely to rotate with respect to the drive sleeve 60", but being retained axially therewith.

The second generally cylindrically portion 86" of the dose dial sleeve 50" comprises a first cylindrical section 88" and a second cylindrical section 90" connected by a radial flange 92 extending from a part of the second section, the first section 88" being rigidly keyed to an inner surface of the first portion 84" of the dose dial sleeve 50", and the second section 90" being of the same outer diameter as the housing 2".

Figure 8:
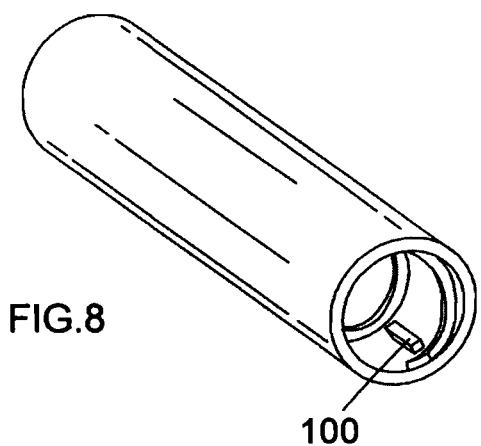
FIG. 8 shows a perspective view of a dose dial sleeve for use in conjunction with the present invention.
Figure 9:
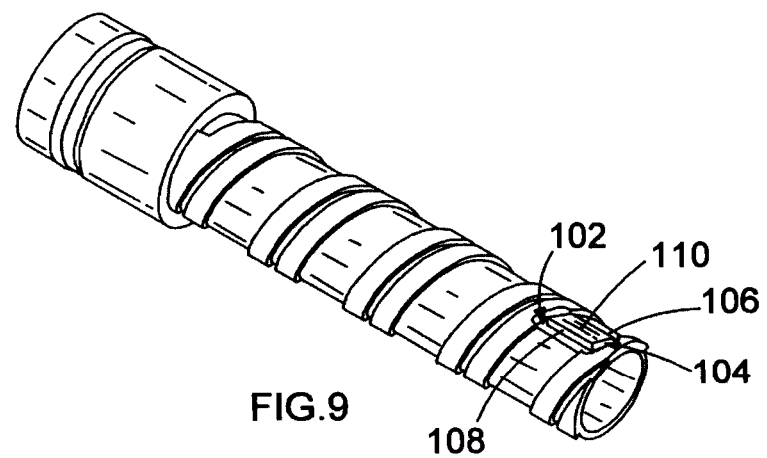
FIG. 9 shows a perspective view of an insert for use with the dose dial sleeve of FIG. 8.

In each of FIGS. 6 and 7, there is a further modification to each of the dose dial sleeve and the insert. This may be seen more clearly with reference to FIGS. 8 and 9.

At a first end of the dose dial sleeve there is located on an internal surface a radially directed lug 100 extending generally parallel to a longitudinal axis of the sleeve. At a second end of the insert on an external surface thereof there is provided a catch means. The catch means comprises a groove 102 extending about a central land 104. The central land 104 is generally wedge shaped such that a first edge 106 nearer the start of the thread extends radially less far than a second opposite edge 108 located further along the thread. A sloping surface 110 is defined between the first edge 106 and the second edge 108. Thus, when the dose dial sleeve is assembled to the insert, by threading the dose dial sleeve onto the insert, the lug 100 passes over the first edge 106 and over the sloping surface 110. As the lug 100 passes fully over the land 104 some elastic deformation of the respective elements, the dose dial sleeve and the insert occurs. Once the lug 100 is over the land 104, the second edge 108 of the land 104 acts as a stop to prevent removal of the dose dial sleeve from the insert.

The location of the second edge 108 of the land 104 is conveniently chosen at a radial location corresponding to 80 units of medicinal product, that is the maximum dose available is 80 units when the dose dial sleeve is wound from the initial position shown in any of FIG. 1, 6 or 7 to a fully extended position with the second edge 108 of the land 104 contacting the lug 100.

Figure 10:
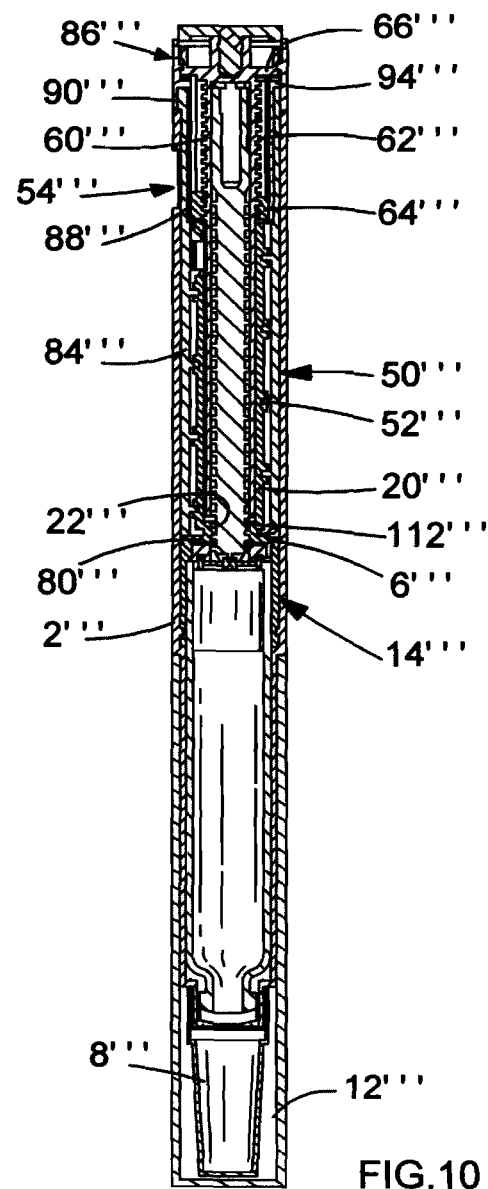
FIG. 10 shows a sectional side view of a fourth embodiment of the drug delivery device in accordance with the present invention.

A fourth embodiment of the present invention is disclosed in FIG. 10. Like reference numerals are used to refer to like parts.

As can be seen the structure of the insert 14''' has been revised. The first side of the web 6''' is substantially unchanged. The other side of the web is now provided with a boss 80'''. A radial flange 112 extends outwardly from the boss 80''', the radial flange 112 being spaced from the web 6''', and a cylindrical portion 20''' extending away from the web 6''' about a periphery of the radial flange 110. A threaded opening 22''' extends through the web 6''' and the boss 80'''.

The dose dial sleeve 50''' is of modified construction. The dose dial sleeve 50''' comprises a first cylindrical portion 84''' rigidly connected to a second generally cylindrical portion 86'''. An inner surface of the first portion 84''' and the outer surface of the cylindrical portion 20''' of the insert 14''' are provided with interengaging features to provide a helical thread 52''' between the insert 14''' and the dose dial sleeve 50'''. An outer surface of the first cylindrical portion 84''' is provided with the dose graphics. The housing 2''' is provided with an aperture or window 54''' through which a portion of the graphics may be viewed.

The second generally cylindrical portion 86''' comprises a first inner cylindrical section 88''' and a second outer cylindrical section 90'''. The first section 88''' is rigidly keyed to an inner surface of the first portion 84''' of the dose dial sleeve 50'''. The second section 90''' is preferably of the same outer diameter as the housing 2'''. Within the dose dial sleeve 50''' there is a radial flange 94 extending between the outer section 90''' and an intermediate part of the inner section 88'''.

A nut 64''' is provided on a helical thread 62''' formed on the drive sleeve 60'''. The nut 64''' is disposed between the drive sleeve 60''' and the second cylindrical section 88''' of the dose dial sleeve 50'''. The second cylindrical section 88''' and the nut 64''' are keyed together by spline means to prevent relative rotation between the nut 64''' and the dose dial sleeve 50'''.

An upper surface of the radial flange 94 of the dose dial sleeve 50''' and a step 66''' of the drive sleeve 60''' are adapted to be releasably engagable with one another to form a clutch means. When, as in FIG. 10, the dose dial sleeve 50''' and the drive sleeve 60''' are not in engagement the dose dial sleeve 50''' is able to rotate with respect to the drive sleeve 60'''. Conveniently, the clutch means comprises a plurality of radially extending longitudinally directed teeth provided respectively on the radial flange 94 of the dose dial sleeve 50''' and the step 66''' of the drive sleeve 60'''. When the dose dial sleeve 50''' and the drive sleeve 60''' are not forced together the respective teeth will ride over one another.

Example 2

Figure 11:
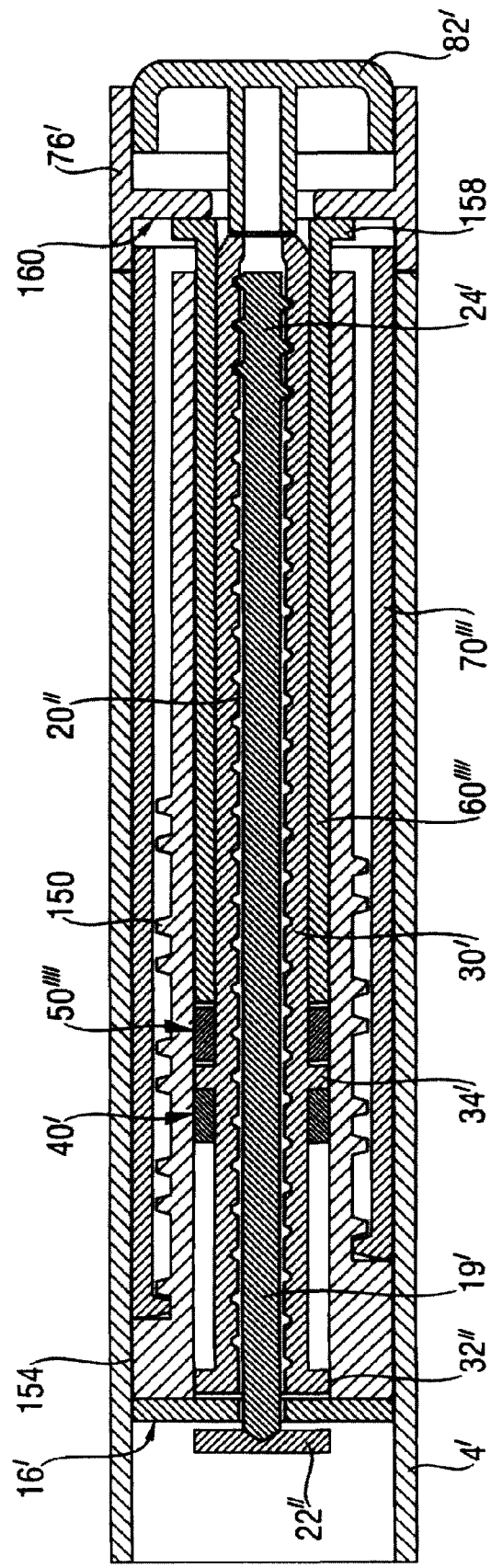
FIG. 11 shows a sectional side view of a fifth embodiment of the drive mechanism according to instant invention in a first, cartridge full, position.

In another embodiment of the invention (FIG. 11) there is seen a drive mechanism comprising a unitary housing 4'. A cartridge, containing medicinal product, can be mounted to the first end of the unitary housing 4' and retained by any suitable means. The cartridge and its retaining means are not shown in the illustrated embodiment. Displacement of the piston causes the medicinal product to be expelled from the cartridge via a needle (also not shown).

An insert 16' is provided within the unitary housing 4'. The insert 16' is secured against rotational and axial motion with respect to the unitary housing 4'. The insert 16' is provided with a threaded circular opening extending therethrough.

An internal housing 154 is also provided within the unitary housing 4'. The internal housing 154 is secured against rotational and axial motion with respect to the unitary housing 4'. The internal housing 154 is provided with a circular opening extending through its length in which a series of longitudinally directed splines are formed. A helical thread 150 extends along the outer cylindrical surface of the internal housing 154. Alternatively, the internal housing may be formed integrally with the insert 16'.

A first thread 19' extends from a first end of a piston rod 20". The piston rod 20" is of generally circular cross-section. The first end of the piston rod 20" extends through the threaded opening in the insert 16' and the first thread 19' of the piston rod 20" is engaged with the thread of the insert 16'. A pressure foot 22" is located at the first end of the piston rod 20". The pressure foot 22" is disposed to abut a cartridge piston (not shown). A second thread 24' extends from a second end of the piston rod 20". The first thread 19' and the second thread 24' are oppositely disposed.

A drive sleeve 30' extends about the piston rod 20". The drive sleeve 30' is generally cylindrical. The drive sleeve 30' is provided at a first end with a first radially extending flange 32". A second radially extending flange 34' is provided, spaced a distance along the drive sleeve 30' from the first flange 32". An external helical thread (not shown) is provided on the outer part of the drive sleeve 30' extending between the first flange 32" and the second flange 34'. An internal helical thread extends along the internal surface of the drive sleeve 30'. The second thread 24' of the piston rod 20" is engaged with the internal helical thread of the drive sleeve 30'.

A nut 40' is located between the drive sleeve 30' and the internal housing 154, disposed between the first flange 32" and the second flange 34' of the drive sleeve 30'. The nut 40' can be either a 'half-nut' or a 'full-nut'. The nut 40' has an internal thread that is engaged with the external helical thread of the drive sleeve 30'. The outer surface of the nut 40' and an internal surface of the internal housing 154 are keyed together by means of longitudinally directed splines to prevent relative rotation between the nut 40' and the internal housing 154, while allowing relative longitudinal movement therebetween.

A clicker 50"" and a clutch 60"" are disposed about the drive sleeve 30', between the drive sleeve 30' and the internal housing 154.

The clicker 50"" is located adjacent the second flange 34' of the drive sleeve 30'. The clicker 50"" includes at least one spring member (not shown). The clicker 50"" also includes a set of teeth (not shown) having a triangular profile disposed towards the second end of the drive mechanism. When compressed, the at least one spring member of the clicker 50""

applies an axial force between the flange 34' of the drive sleeve 30' and the clutch 60''''. The outer surface of the clicker 50'''' and an internal surface of the internal housing 154 are keyed together by means of longitudinally directed splines to prevent relative rotation between the clicker 50'''' and the internal housing 154, while allowing relative longitudinal movement therebetween.

The clutch 60'''' is located adjacent the second end of the drive sleeve 30'. The clutch 60'''' is generally cylindrical and is provided at its' first end with a plurality of teeth of triangular profile disposed about the circumference (not shown), that act upon the teeth of the clicker 50''''. Towards the second end of the clutch 60'''' there is located a shoulder 158. The shoulder 158 of the clutch 60'''' is disposed between the internal housing 154 and a radially inwardly directed flange of the dose dial grip 76' (described below). The shoulder 158 of the clutch 60'''' is provided with a plurality of dog teeth (not shown) extending in the direction of the second end of the drive mechanism. The clutch 60'''' is keyed to the drive sleeve 30' by way of splines (not shown) to prevent relative rotation between the clutch 60'''' and the drive sleeve 30'.

A dose dial sleeve 70''' is provided outside of the internal housing 154 and radially inward from the unitary housing 4'. A helical thread is provided on an inner surface of the dose dial sleeve 70'''. The helical thread of the dose dial sleeve 70''' is engaged with the helical thread 150 of the internal housing 154.

The unitary housing 4' is provided with a window (not shown) through which part of the outer surface of the dose dial sleeve 70''' may be viewed. Conveniently, a visual indication of the dose that may be dialed, for example reference numerals (not shown), is provided on the outer surface of the dose dial sleeve 70'''. Conveniently, the window of the unitary housing 4' allows only the dose that is currently dialed to be viewed.

A dose dial grip 76' is located towards the second end of the drive mechanism. The dose dial grip 76' is secured against rotational and axial motion within respect to the dose dial sleeve 70'''. The dose dial grip 76' is provided with a radially inwardly directed flange 160. The radially inwardly directed flange 160 of the dose dial grip 76' is provided with a plurality of dog teeth (not shown) extending in the direction of the first end of the drive mechanism to abut the dog teeth of the clutch 60''''. Coupling and decoupling of the dog teeth of the dose dial grip 76' with the dog teeth of the clutch 60'''' provides a releasable clutch between the dose dial grip 76' and the clutch 60''''.

A button 82' of generally 'T' shaped cross-section is provided at a second end of the drive mechanism. A cylindrical feature of the button 82' extends towards the first end of the drive mechanism, through an opening in the dose dial grip 76' and into a recess in the drive sleeve 30'. The cylindrical feature of the button 82' is retained for limited axial movement in the drive sleeve 30' and against rotation with respect thereto. The cylindrical feature of the button 82' has lugs extending radially (not shown) that abut the second surface of the shoulder 158 of the clutch 60''''. The second end of the button 82' is generally circular and has a cylindrical skirt about its periphery that descends towards the first end of the drive mechanism. The skirt of the button 82' is located radially inward from the dose dial grip 76'.

To dial a dose, a user rotates the dose dial grip 76'. The spring member of the clicker 50'''' applies an axial force to the clutch 60'''' in the direction of the second end of the drive mechanism. The force exerted by the spring member of the clicker 50'''' couples the dog teeth of the clutch 60'''' to the dog teeth of the dose dial grip 76' for rotation. As the dose dial grip 76' is rotated, the associated dose dial sleeve 70''', the drive sleeve 30' and the clutch 60'''' all rotate in unison.

Audible and tactile feedback of the dose being dialed is provided by the clicker 50'''' and the clutch 60''''. As the clutch 60'''' is rotated, torque is transmitted from the teeth at the first end of the clutch 60'''' and the teeth of the clicker 50''''. The clicker 50'''' cannot rotate with respect to the internal housing 154, so the at least one spring member of the clicker 50'''' deforms allowing the teeth of the clutch 60'''' to jump over the teeth of the clicker 50'''' producing an audible and tactile 'click'. Preferably, the teeth of the clicker 50'''' and the teeth of the clutch 60'''' are disposed such that each 'click' corresponds to a conventional unit of the medicinal product, or the like.

The helical thread of the dose dial sleeve 70''' and the internal helical thread of the drive sleeve 30' have the same lead. This allows the dose dial sleeve 70''' to advance along the thread 150 of the internal housing 154 at the same rate as the drive sleeve 30' advances along the second thread 24' of the piston rod 20''. Rotation of the piston rod 20'' is prevented due to the opposing direction of the first thread 19' and the second thread 24' of the piston rod 20''. The first thread 19' of the piston rod 20'' is engaged with the thread of the insert 16' and so the piston rod 20'' does not move with respect to the unitary housing 4' while a dose is dialed.

The nut 40', keyed to the internal housing 154, is advanced along the external thread of the drive sleeve 30' by the rotation of the drive sleeve 30'. When a user has dialed a quantity of medicinal product that is equivalent to the deliverable volume of the cartridge, the nut 40' reaches a position where it abuts the second flange 34' of the drive sleeve 30'. A radial stop formed on the second surface of the nut 40' contacts a radial stop on the first surface of the second flange 34' of the drive sleeve 30', preventing both the nut 40' and the drive sleeve 30' from being rotated further.

Should a user inadvertently dial a quantity greater than the desired dosage, the drive mechanism allows the dosage to be corrected without dispense of medicinal product from the cartridge. The dose dial grip 76' is counter-rotated. This causes the system to act in reverse. The torque transmitted through the clutch 60'''' causes the teeth at the first end of the clutch 60'''' to ride over the teeth of the clicker 50'''' to create the clicks corresponding to the dialed dose reduction.

When the desired dose has been dialed, the user may then dispense this dose by depressing the button 82' in the direction of the first end of the drive mechanism. The lugs of the button 82' apply pressure to the second surface of the shoulder 158 of the clutch 60'''', displacing the clutch 60'''' axially with respect to the dose dial grip 76'. This causes the dog teeth on the shoulder 158 of the clutch 60'''' to disengage from the dog teeth of the dose dial grip 76'. However, the clutch 60'''' remains keyed in rotation to the drive sleeve 30'. The dose dial grip 76' and associated dose dial sleeve 70''' are now free to rotate (guided by the helical thread 150 of the internal housing 154).

The axial movement of the clutch 60'''' deforms the spring member of the clicker 50'''' and couples the teeth at the first end of the clutch 60'''' to the teeth of the clicker 50'''' preventing relative rotation therebetween. This prevents the drive sleeve 30' from rotating with respect to the internal housing 154, though it is still free to move axially with respect thereto.

Pressure applied to the button 82' thus causes the dose dial grip 76' and the associated dose dial sleeve 70''' to rotate into the unitary housing 4'. Under this pressure the clutch 60'''', the clicker 50'''' and the drive sleeve 30' are moved axially in the direction of the first end of the drive mechanism, but they do not rotate. The axial movement of the drive sleeve 30' causes the piston rod 20" to rotate though the threaded opening in the insert 16', thereby to advance the pressure foot 22". This applies force to the piston, causing the medicinal product to be expelled from the cartridge. The selected dose is delivered when the dose dial grip 76' returns to a position where it abuts the unitary housing 4'.

When pressure is removed from the button 82', the deformation of the spring member of the clicker 50"" is used to urge the clutch 60"" back along the drive sleeve 30' to re-couple the dog teeth on the shoulder 158 of the clutch 60"" with the dog teeth on the dose dial grip 76'. The drive mechanism is thus reset in preparation to dial a subsequent dose.

What is claimed is:

1. A method of assembling a drug delivery device comprising the steps of
    a) providing a single one piece unitary housing having a first end and a second end, a cartridge, a drive mechanism, a dose dial mechanism, and optionally a drug delivery mechanism; and
    b) inserting or introducing into the second end of the unitary housing the cartridge, the drive mechanism, the dose dial mechanism, and optionally the drug delivery mechanism, whereby said cartridge, said drive mechanism, said dose dial mechanism, and optionally said drug delivery mechanism are not mechanically engaged with the said unitary housing,
    wherein the unitary housing forms a single drug delivery outer housing that covers the cartridge, the drive mechanism, the dose dial mechanism, and optionally the drug delivery mechanism of the drug delivery device after assembly and allows delivery of a set dose of a drug to be dispensed through the first end of the one piece unitary housing.

2. The method of assembling a drug delivery device according to claim 1, wherein the cartridge is first inserted or introduced into the unitary housing followed by insertion or introduction of the drive mechanism, the dose dial mechanism, and optionally the drug delivery mechanism into the unitary housing.

3. The method of assembling a drug delivery device according to claim 2, wherein one or more components of the drug delivery device are pre-assembled or modular.

4. The method of assembling a drug delivery device according to claim 2, wherein one or more components of the drug delivery device, selected from the cartridge, the drive mechanism, the dose dial mechanism, and optionally the drug delivery mechanism, or components of said cartridge, drive mechanism, dose dial mechanism, or drug delivery mechanism, are pre-assembled or modular.

5. The method of assembling a drug delivery device according to claim 2, wherein the unitary housing is of pen-type or non-pen type shape.

6. The method of assembling a drug delivery device according to claim 2, wherein the cartridge comprises a pharmaceutical formulation for subcutaneous or intramuscular administration.

7. The method of assembling a drug delivery device according to claim 1, wherein one or more components of the drug delivery device are pre-assembled or modular.

8. The method of assembling a drug delivery device according to claim 1, wherein one or more components of the drug delivery device, selected from the cartridge, the drive mechanism, the dose dial mechanism, and optionally the drug delivery mechanism, or components of said cartridge, drive mechanism, dose dial mechanism, or drug delivery mechanism, are pre-assembled or modular.

9. The method of assembling a drug delivery device according to claim 1, wherein the unitary housing is of pen-type or non-pen type shape.

10. The method of assembling a drug delivery device according to claim 1, wherein the cartridge comprises a pharmaceutical formulation for subcutaneous or intramuscular administration.

11. The method of assembling a drug delivery device according to claim 1, wherein
    the cartridge comprises insulin or a derivative or analogue thereof.

12. The method of assembling a drug delivery device according to claim 1, wherein the cartridge comprises heparin or a derivative or analogue thereof.

13. A drug delivery device assembled according to the method according to claim 1.

14. The drug delivery device according to claim 13, which is a pen-type or a nonpen-type injector.

15. The drug delivery device according to claim 13, comprising a pharmaceutical formulation for subcutaneous or intramuscular administration.

16. The drug delivery device according to claim 13, comprising insulin or a derivative or analogue thereof.

17. The drug delivery device according to claim 13, comprising heparin or a derivative or analogue thereof.

18. The method of assembling a drug delivery device according to claim 1, wherein
    a cap is releasably secured to the first end of the unitary housing to cover a needle unit of the drug delivery device.

* * * * *